United States Patent [19]

Brossi et al.

[11] Patent Number: 4,900,748

[45] Date of Patent: Feb. 13, 1990

[54] CARBAMATES RELATED TO (−)-PHYSOSTIGMINE AS CHOLINERGIC AGENTS

[75] Inventors: Arnold Brossi, Bethesda, Md.; Qian-Sheng Yu, Washington, D.C.; John R. Atack, Bethesda, Md.; Stanley I. Rapoport, Washington, D.C.

[73] Assignee: The United States of America as represented by the Department of Health and Human Services, Washington, D.C.

[21] Appl. No.: 166,825

[22] Filed: Mar. 4, 1988

[51] Int. Cl.$^4$ .................. A61K 31/40; C07D 487/00
[52] U.S. Cl. ...................... 514/411; 548/429
[58] Field of Search .................. 548/429; 514/411

[56] References Cited

U.S. PATENT DOCUMENTS

| | | | |
|---|---|---|---|
| 2,909,530 | 10/1959 | Rudner | 548/428 |
| 4,278,667 | 7/1981 | Madison et al. | 548/428 |
| 4,278,679 | 7/1981 | Madison et al. | 548/428 |
| 4,647,580 | 3/1987 | Roszkowski | 548/428 |
| 4,661,509 | 4/1987 | Gordon et al. | 548/428 |

FOREIGN PATENT DOCUMENTS 116238 12/1983 European Pat. Off. ............ 548/428

OTHER PUBLICATIONS

Kawabuchi, et al., Synapse, vol. 2, pp. 139–147 (1988).
Yu, et al., Heterocycles, vol. 27, No. 3, (1988) pp. 745–750.
Yu, et al., FEBS Letters, vol. 234, No. 1, pp. 127–130, (1988).
Chemical Abstracts 102:214989c (1985).
Chemical Abstracts 105:72467s (1986).

*Primary Examiner*—John M. Ford
*Assistant Examiner*—Robert C. Whittenbaugh
*Attorney, Agent, or Firm*—Browdy and Neimark

[57] ABSTRACT

Highly potent analogs of (−)-physostigmine are provided which are potent inhibitors of acetylcholinesterase and butyrylcholinesterase. These compounds are useful in treatment of glaucoma, Alzheimer's disease, myasthenia gravis, and organophosphate poisoning.

13 Claims, 3 Drawing Sheets

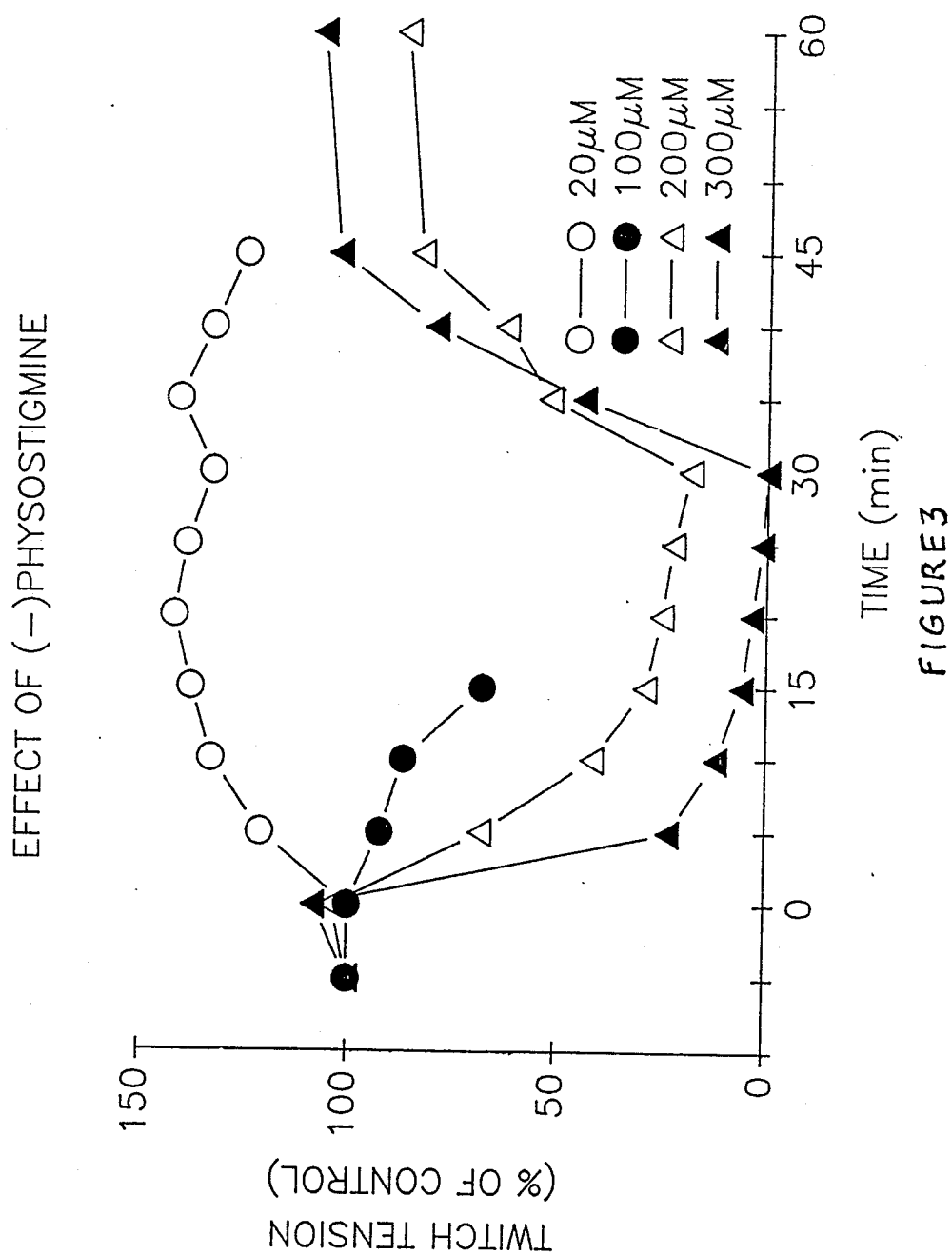

CARBAMATES RELATED TO (−)-PHYSOSTIGMINE AS CHOLINERGIC AGENTS

FIELD OF THE INVENTION

The present invention relates to improvements in the treatment of diseases, and more particularly to compounds which are potent inhibitors of acetylcholinesterase and butyrylcholinesterase.

BACKGROUND OF THE INVENTION

Physostigmine, also called esrine, and certain of its derivatives are well known anticholinesterase inhibitors, and are useful in the treatment of glaucoma, Myasthenia Gravis, Alzheimer's disease, and as an antidote against poisoning with organophosphates.

Physostigmine was first isolated in 1864 by Jobst and Hesse after it was originally introduced into England in the form of the Calabar bean in 1840 by Daniell, a British medical officer. During the last century, physostigmine has been used as a treatment for glaucoma, and in the reversal of atropine-induced coma. More recently, physostigmine has been used effectively as an antidote to several drugs possessing central anticholinergic properties.

In the last fifteen years, the knowledge of receptor function has been advanced considerably by studies for the acetylcholine-receptor-ion-channel complex (AChR) of the neuromuscular junction. The occurrence of nicotinic AChRs at very high densities in Torpedo and Electrophorus electric organs made this membrane receptor easily available for study. In addition, specific chemical probes for the different active sites have contributed significantly to understanding of the morphology and function of this receptor.

In the early 1970's, alpha-bungarotoxin (alpha-PGT) was isolated from snake venoms and was found to bind irreversibly and specifically to the acetylcholine (ACh) recognition site on the nicotinic acetylcnoline-receptor-ion-channel complex. The availability of such a highly selective probe permitted the isolation, purification, functional reconstitution into artificial lipid membranes and, ultimately, cloning of the different subunits which comprise the nicotinic acetylcholine-receptor-ion-channel complex.

The pharmacological charactization of another class of toxins, the histrionicotoxins, isolated from the skin secretion of frogs of the family Dendrobatidae, disclosed an important new class of sites on the nicotinic AChR. These sites, which are distinct from the agonist recognition site and are most likely located on the ion channel component of the AChR, are responsible for allosteric alterations or noncompetitive blockage of neuromuscular transmission. Drugs with distinct and well-known pharmacological activities on the peripheral as well as central nervous systems, such as tricyclic antidepressants, phenothiazine antipsychotics, the hallucunogenic agent phencyclidine (PCP), local anesthetics, antimuscarinics, anticholinesterase agents, and may other have been shown to modify noncompetitively the activation of the AChR.

Additionally, microscopic kinetic models are now available for study. More refined biophysical techniques, such as the patch-clamp method which allows the recording of single-channel currents, have disclosed finer aspects of the permeability changes initiated by the binding of the agonist molecules.

On the biochemical front, rapid-mixing methods have been used to measure accurately early conformational transitions of nicotinic receptor molecules. These studies showed that activation of the nicotinic AChR comprises complex microscopic gating kinetics, i.e. the conformational changes of the protein may involve transitions through many states, on different time scales, and with distinct voltage dependencies.

It has been reported that the agonist recognition site at the nicotinic acetylcholine receptor has strong stereospecificity, as revealed by the optical isomers of certain semi-rigid agonists, cf. Spivak et al., *Mol. Pharmacol.* 23: 337–343, 1983. The ion channel sites, on the other hand seemed not to be stereospecific, as revealed by the similar qualitative and quantitative actions of the enantiomers of perhydrohistrionicotoxin at the nicotinic AChR, cf. Spivak et al., *FEBS Lett.* 163: 189–193, 1983.

The natural isomer of physostigmine has shown blocking as well as agonist properties at the neuromuscular AChR, whereas (+)-physostigmine has negligible ChE inhibitory activity, as reported by Brossi et al., *FEBS Lett.* 201: 190–192, 1986. In protection studies in rats, (+)-physostigmine was found most effective as a pretreatment drug against multiple lethal doses of sarin, cf. Albuquerque et al., *Fundam. Appl. Toxicol.* 5: 182–203, 1985. It appears that direct interactions of the carbamates with the postsynaptic nicotinic AChR may account for their beneficial effects in the observed protection. The effectiveness of these carbamates in protecting against organo-phosphates appears to be directly related to the ability of the former to decrease the hyperactivation caused by the accumulation of the neurotransmitter. The evidence acquired from such studies is of fundamental importance in the assessment of new drugs in the treatment of cholinergic disorders, including myasthenia gravis and Alzheimer's disease. Beneficial results are more likely to be achieved with cholinergic agonists resistant to ChE inhibition and those crossing the blood-brain barrier.

SUMMARY OF THE INVENTION

It is an object of the present invention to overcome the deficiencies of the prior art, such as noted above.

It is another object of the present invention to provide highly potent analogs of physostigmine.

It is a further object of the present invention to provide improvements in therapy relative to diseases such as glaucoma, myasthenia gravis, Alzhemier's disease, and organophosphate poisoning.

It is yet a further object of the present invention to provide compounds with pronounced acetylcholinesterase and butyrylcholinesterase activity.

The (−) compounds of the present invention have the following formulae:

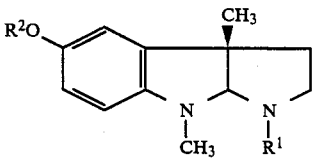

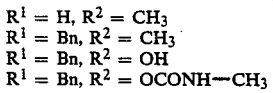

$R^1$ = H, $R^2$ = $CH_3$
$R^1$ = Bn, $R^2$ = $CH_3$
$R^1$ = Bn, $R^2$ = OH
$R^1$ = Bn, $R^2$ = OCONH—$CH_3$

-continued
R¹ = CH₂=CH—CH₂, R² = CONHCH₃
R¹ = CH₂—CH₂—Ph, R² = CONUCH₃

DETAILED DESCRIPTION OF THE INVENTION

Figure 1:
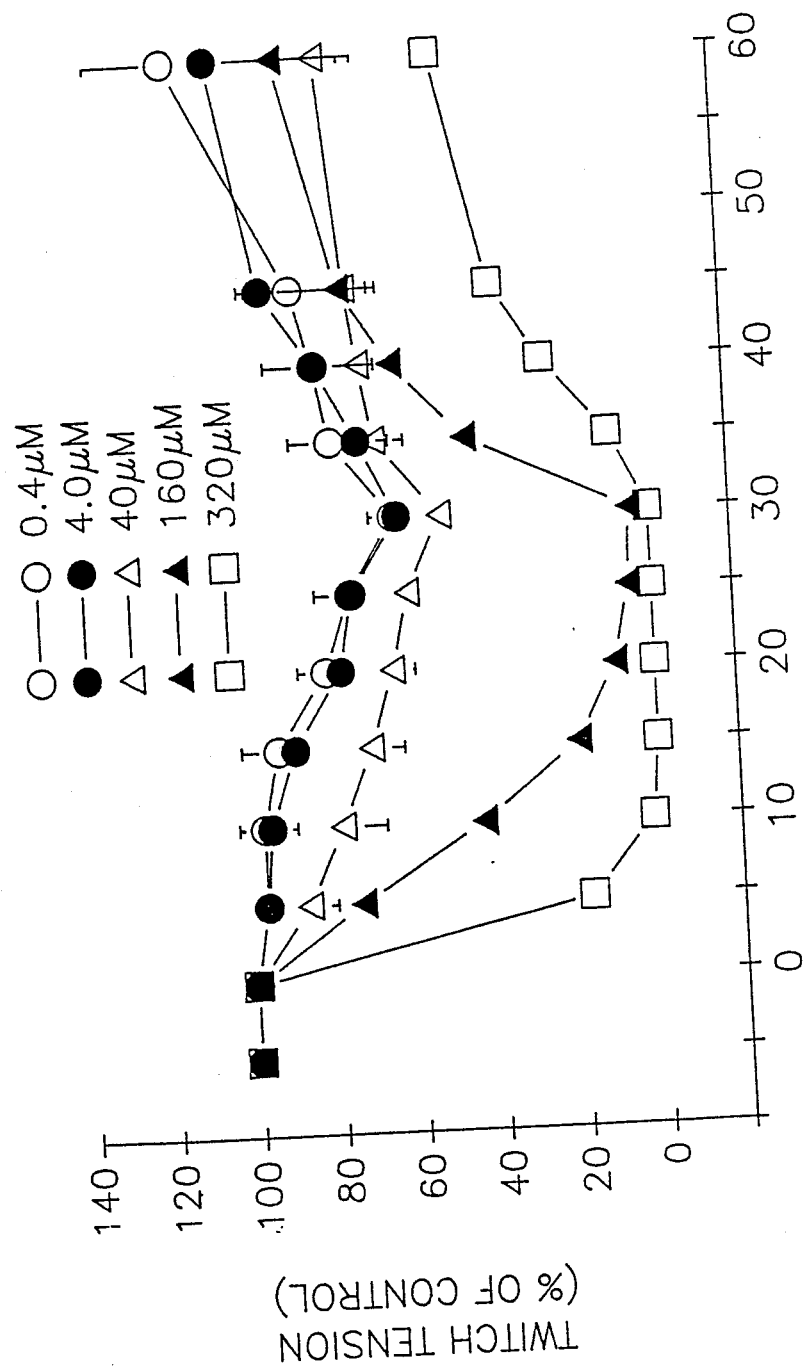
Figure 2:
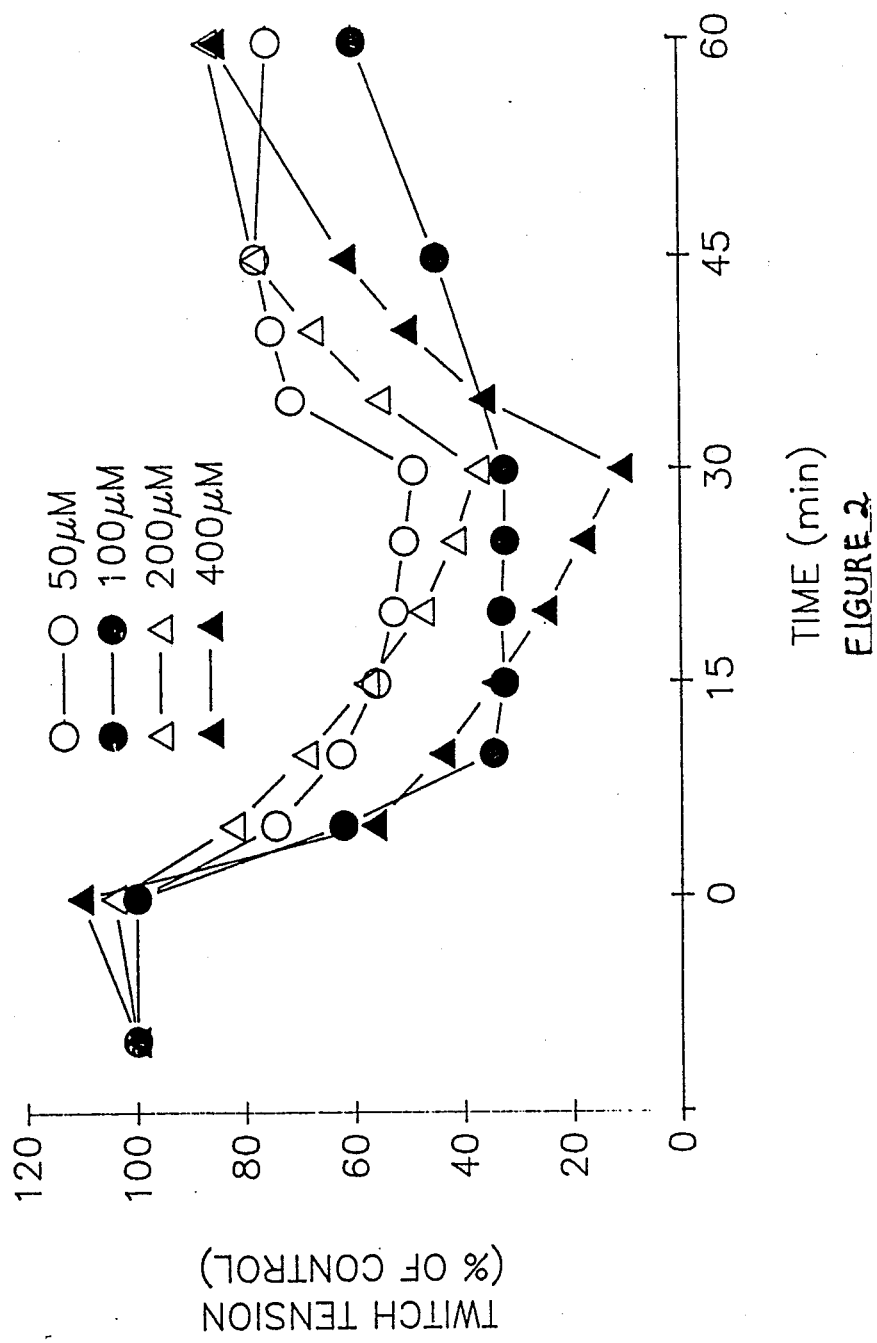

The compounds of the (−) series, shown above, were made from commercially available (−)-physostigmine obtained from Aldrich Chemical Co., giving (−)-eseroline in high yield and excellent optical purity, cf. Yu et al., *Heterocycles*, 26: 1271, 1987.

The carbamates of the present invention were prepared from (−)-eseroline and isocyanates in ether in the presence of a catalytic amount of sodium. The carbamates were purified by chromatography on a silica gel column and were eluted with 9:1 methylene chloride:-methanol. The compounds were chromatographically pure.

The compounds of the (−)-series which have different N1-substitution were made from totally synthetic (−)-N-noreseroline O-methyl ether prepared from the more polar amorphous urea with $[\alpha]_d = -40°$ (c=1.7, CHCl₃) by the procedure of Schönenberger et al., *Helv. Chim. Acta*, 69: 1480, 1986. N-benzylation afforded the (−)-N-benzyl-erserolin-O-methyl ether which, after O-debenzylation with BBr₃, gave N1-benzylnoreseroline. After reaction with isocyanates, the N1-benzylated carbamate was formed. Catalytic debenzylation with Pd(OH)₂ catalyst in methanol yielded N1-norphysostigmine and after reaction of the former with allyl bromide, N(1)-allyl-N(1)-norphysostigmine.

The Julian total synthesis of natural (−)-physostigmine (Julian et al., *J. Amer. Chem. Soc.*, 57: 755, 1935) in principle also yields the unnatural (+)-isomer when carried through with the proper optically active intermediate. It was also shown that this process yields pure material only after several crystallizations and in low yield (*Pharm. Pharmacol.*, 22: 389, 1970).

An alternative method of making the compounds of the present invention, involving an improved cyclization of oxindoles to tricyclic endoleninepyrrolizines, is also the subject of the present invention. This method includes cyclizing the oxindoles with lithium aluminum hydride under reflux. The reaction is preferably conducted under nitrogen atmosphere.

O-Methyl-N(1)-noreseroline

Fifty milligrams (0.22 mmol) of the following compound

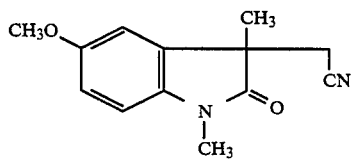

(50 mg, 0.22 mmol) was dissolved in 5 ml tetrahydrofuran, and 33 mg (0.44 mmol) lithium aluminum hydride was added. The reaction mixture was first stirred under nitrogen atmosphere for one hour, and then heated to reflux. After the solution was refluxed for five minutes, the solvent was evaporated and the residue was dissolved in 2 ml 2N HCl. The acidic aqueous solution was washed with 20 ml diethyl ether, and basified by sodium carbonate, then extracted three times with 20 ml of diethyl ether. The ether extract was dried with magnesium sulfate and concentrated to about 2 ml, which was added to a saturated ethanolic solution of 30 grams fumaric acid. Crystallization yielded crystalline fumarate of the following compound:

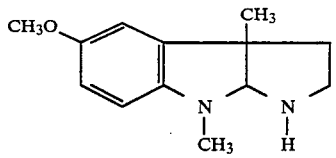

67 mg, 91%; mp 177°–178° C.; mp 1.97°–178° C.; MS(CI), m/z 219 M++1); ¹H—NMR CD₂O): 6.87-6.95 (m, 2H, C4—H and C6—H), 6.69 (m, 1H, C7—H), 5.09 (s, 1H, C9—H), 3.79 (s, 3H, O—CH₃), 3.20–3.60 (m, 2H, C—H₂) 3.09 (s, 3H, N8—CH₃) 2.85 (br. 3H, N1—CH₃), 2.39 (m, 2H, C3—H2), 1.49 (S, 3H, C10—CH₃). Anal. Calc. for C₁₃H₁₈N₂O.C₄H₄O₄: C, 61.06; H, 6.63; N. 8.38. Found: C. 60.96; H, 6.67; N. 8.37. Identical by TLC and melting point with a reference sample.

The resultant carbamate (−) compounds can be converted into salts such as fumarates, salicylates, oxalates, and the like, which often are crystalline compounds and are water soluble. The free bases are soluble in aqueous ethanol, propylene glycol, DMSO, and like solvents.

The carbamates of the present invention can be used transdermally or injected as oily or ethanolic solutions. For oral dosage, the carbamates are preferably converted to a suitable pharmaceutically acceptable salt such as a fumarate, succinate, salicylate hydrochloride, or the like.

(−)-N(1)-O-Methylnoreseroline

Eight grams of sodium was dissolved in 350 ml pentanol. After the sodium was no longer visible, 7.86 grams (21.5 mmol) of more polar urea was added and the reaction mixture was refluxed for two hours in nitrogen atmosphere. After evaporation of the solvent in vacuo, the residue was dissolved in 150 ml water, extracted with diethyl ether (twice with 200 ml. twice with 100 ml). The ether extracts were combined, washed with 50 ml brine, dried over sodium sulfate, concentrated, and three grams of a saturated ethanolic solution of fumaric acid was added to give the fumarate salt. The yield was 6.78 grams (93.4%), mp 199°–200° C.; $[\alpha]_D - 68.2°$ (c=0.5, methanol).

(−)-N(1)-Benzyl-noreseroline

The compound prepared as above (21.3 g, 4.22 mmol) was dissolved in 20 ml of methylene chloride, and 20 ml of a 1.0M solution of BBr₃ in methylene chloride was added dropwise with stirring. The reaction mixture was stirred for one hour at room temperature in a nitrogen atmosphere. After the solvent was evaporated, the residue was dissolved in 20 ml methanol and stirred for five minutes. The solvent was evaporated, and the residue was dissolved in 20 ml water which was basified by sodium bicarbonate, extracted with diethyl ether, twice with 100 ml and twice with 50 ml, washed with 50 ml brine, and dried over sodium sulfate. Evaporation of the solvent gave 1.2 g, 96.7% yield of (−)-N(1)-Benzyl-noresceroline as a foam; $[\alpha]D - 60.2°$ (c=1, CHCl₃).

(−)-N(1)-Benzyl-norphysostigmine 2.47 g (8.39 mmol) (−)-N(1)-benzylnoreseroline was dissolved in 200 ml of anhydrous diethyl ether, and five pieces of sodium, each about five mg, were added. After stirring for 1.5 minutes at room temperature, 0.57 g (10.07 mmol) methylisocyanate was added dropwise over a period of five minutes, and another 0.57 g of methylisocyanate was added. The mixture was stirred for 30 minutes at room temperature under a nitrogen atmosphere. After the solvent was evaporated, the residue was flash chromatographed on a silica gel column (100:1 methylene chloride/methanol) to give (−)-N(1)-benzyl-norphysostigmine as a gum in 71.43% yield, 2.1 g; $[\alpha]D-35.6°$ (c=1.5, CHCl$_3$).

(−)-N(1)-Norphysostigmine (−)-N(1)-benzyl-norphysostigmine, 2.1 g (5.97 mmol) was dissolved in 200 ml methanol, and 40 mg of palladium hydroxide on carbon was added. After hydrogenation under atmospheric pressure for one hour, the palladium catalyst was filtered through celite, and the solvent was evaporated in vacuo. The residue was dissolved in 20 ml diethyl ether and 0.5 ml ethanol to make a clear solution, to which was added a saturated alcoholic solution of 830 g fumaric acid. The mixture was kept in a refrigerator overnight, after which a crude fumarate of (−)-N(1)-norphysostigmine was obtained, which was recrystallized from ethanol to give the fumarate of (−)-N(1)-norphysostigmine as white crystals in 74.20% yield, 1.68 g; mp 178°-180° C.; $[\alpha]D-65.8°$ (c=1. methanol).

(−)-N(1)-Allylphsostigmine

The fumate of (−)-N(1)-norphysostigmine (200 mg, 0.53 mmol) and 100 mg potassium carbonate were added to 10 ml methyl cyanide. Then 1 ml allyl bromide was added to the mixture, which was stirred at room temperature in a nitrogen atmosphere for four hours. After the solvent was evaporated, the residue was flash chromatographed on a silica gel column (100:1 methylene chloride/methanol) to yield (−)-N(1)-allylphysostigmine as a gum in 62.0% yield, 99 mg; $[\alpha]D-95.3°$ (c=0.5, CHCl$_3$).

Twenty mg of (−)-N(1)-allylphysostigmine was dissolved in 1 ml ethanol, and 1 ml of an ether solution of 11 mg salicyclic acid was added to the above solution. The solution remained in the refrigerator overnight, after which time the salicylate of (−)-N(1)-allylphysostigmine as white crystals in 78.86% yield, 23 mg; mp 72°-74° C.; $[\alpha]D-100.9$ (c=1, ethanol, CHCl$_3$). The analysis calculated for $C_{17}H_{23}N_3O_2 \cdot C_7H_6O_3 \cdot \frac{1}{2}H_2O$: C, 64.26; H, 6.62; N, 9.37. Found: C, 64.54; H, 6.73; N, 9.33.

(−)-N(1)-Phenylethylphysostigmine

The fumarate of (−)-N(1)-norphysostigmine, 200 mg (0.53 mmol) and 100 mg of potassium carbonate were added into 10 ml of methylcyanide, then 2 mg of 2-bromoethylbenzene and potassium iodide were added. The mixture was stirred for sixty hours at room temperature under nitrogen. The solvent was evaporated, and the resulting brown residue was flash chromatographed on a silica gel column (100:1 methylene chloride/methanol) to give (−)-N(1)-phenylethylphysostigmine as a foam in 26% yield, 50 mg; $[\alpha]_D-152.5°$ (c−1, CHCl$_3$).

(−)-4-Chlorophenyl carbamoyl-eseroline was prepared from (−)-eseroline and 4-chlorophenyl isocyanate. The melting point of the product was 186°-190° C.; $[\alpha]_D-71.9°$ (c=0.1, CHCl$_3$).

(−)-4-Methoxyphenyl (carbamoyl) eseroline was prepared as above from (−)-eseroline and 4-methoxyphenylisocyanate; mp 182°-183°, $[\alpha]_D=67.5°$ (c=0.1, CHCl$_3$).

TABLE 1

| Compound | Acetylcholinesterase | | | | Butyrylcholinesterase | |
|---|---|---|---|---|---|---|
| | Cortex | Caudate | RBC | Eel | Cortex | Plasma |
| (−) physo | 34 ± 10 | 40 ± 14 | 29 ± 9 | 61 ± 18 | 140 ± 60 | 14 ± 6 |
| YU-79 | 36 ± 3 | 21 ± 1 | 24 ± 6 | 350 ± 90 | 2,500 ± 1,100 | 1,300 ± 400 |
| YU-71 | 15 ± 1 | 12 ± 10 | 16 ± 4 | 110 ± 110 | 8.7 ± 3.7 | 3.6 ± 1.0 |
| YU-69-1 | 24 ± 5 | 27 ± 10 | 26 ± 8 | 460 ± 80 | 20 ± 11 | 2.7 ± 1.6 |
| Methyl physo | 260 ± 60 | 200 ± 40 | 210 ± 40 | 970 ± 260 | 3,100 ± 600 | 420 ± 120 |
| YU-94 | 195 ± 97 | 218 ± 109 | 331 ± 95 | 998 ± 455 | 54.2 ± 19.0 | 10.5 ± 3.8 |
| YU-96 | 22.4 ± 0.8 | 18.5 ± 0.9 | 20.6 ± 0.3 | 56.3 ± 1.8 | 34.9 ± 16.9 | 1.82 ± 0.74 |
| YU-110 | 31.7 ± 10.2 | 40.8 ± 18.7 | 44.7 ± 26.0 | 69.2 ± 25.3 | 15.6 ± 6.9 | 2.65 ± 2.01 |
| YU-112 | 155 ± 28 | 191 ± 56 | 213 ± 38 | 1031 ± 409 | 7.00 ± 0.34 | 1.59 ± 0.51 |
| YU-114 | 229 ± 40 | 276 ± 9 | 347 ± 10 | 1680 ± 380 | 224 ± 47 | 27.6 ± 1.8 |
| YU-116 | 417 ± 88 | 448 ± 29 | 654 ± 32 | 1800 ± 85 | 4460 ± 1290 | 4000 ± 52 |
| YU-117 | 37.1 ± 6.6 | 28.3 ± 3.7 | 29.4 ± 5.2 | 33.5 ± 0.6 | 1140 ± 170 | 191 ± 61 |
| YU-120 | 20.8 ± 3.7 | 20.3 ± 6.8 | 17.6 ± 9.1 | 152 ± 9 | 16.0 ± 4.4 | 4.13 ± 1.25 |

YU-79 = eseroline phenylcarbamate
YU-71 = eseroline octylcarbamate
YU-69-1 = eseroline benzylcarbamate
YU-94 = N—benzylphysostigmine
YU-96 = N—norphysostigmine
YU-110 = N—allyl physostigmine
YU-112 = N—phenylethyl physostigmine
YU-114 = methoxyphenyl carbamoyleseroline
YU-116 = chlorophenyl carbamoyleseroline
YU-117 = methosulfate of (−)physostigmine
YU-120 = butylcabamoyl eseroline Of the 8 compounds evaluated (YU-94, 96, 110, 112, 114, 116, 117 and 120), 5 are N-substituted analogues of physostigmine (they have modifications to the ring structure of physostigmine; YU-94, 96, 110, 112 and 117) and 3 (YU-114, 116 and 120) are analogues similar to the compounds previously found to have interesting anticholinesterase properties. Thus, YU-114 and YU-116 have the same structure as YU-79 (phenyl carbamoyleseroline) with the addition of a methoxy group and a chloride ion, respectively, to the phenyl group and YU-120 is the same as YU-71 (octyl carbamoyleseroline except that the octyl group has been replaced by a butyl group.

As shown in Table 1, the compounds of the present invention were evaluated for acetylcholinesterase activity and butyrylcholinesterase activity. Of these compounds evaluated, five are N-substituted analogs of physostigmine, i.e., they have modifications to the ring structure of physostigmine: YU-94, 96, 110, 112, and 117. Three of these compounds, YU-114, 116, and 120, are analogs which are similar to compounds which have previously been found to have interesting anticholinesterase properties. YU-114 and YU-116 have the same structure as phenyl carbamoyleseroline with the addition of a methoxy group and a chloride ion, respectively, to the phenyl group. YU-120 is the same as octyl carbamoyleseroline except that the octyl group has been replaced by a butyl group.

Table 2 shows the acetylcholinesterase and butyrylcholinesterase activity of the natural and unnatural physostigmine compounds of interest.

TABLE 2

| | IC50's, nM | | | | | |
|---|---|---|---|---|---|---|
| | ACETYLCHOLINESTERASE | | | | BUTYRYLCHOLINESTERASE | |
| | Cortex | Caudate | RBC | Eel | Cortex | Plasma |
| (+/−)physo | 72–28 | 72–14 | 83–28 | 92–40 | 270–150 | 35–7 |
| (−)physo | 34–10 | 40–14 | 29–9 | 61–18 | 140–60 | 14–6 |
| (+)physo | 22,000 | 26,000 | 25,000 | 53,000 | 26,000 | 4,000–100 |
| (+/−)eseroline | >10,000 | >10,000 | >10,000 | >10,000 | >10,000 | >10,000 |
| (−)eseroline | >10,000 | >10,000 | >10,000 | >10,000 | >10,000 | >10,000 |
| (+)eseroline | >10,000 | >10,000 | >10,000 | >10,000 | >10,000 | >10,000 |
| YU-71 | 15–1 | 12–10 | 16–4 | 110–110 | 8.7–3.7 | 3.6–1.0 |
| YU-69-1 | 24–5 | 27–10 | 26–8 | 460–80 | 20–11 | 2.7–1.6 |
| OTHER ANTICHOLINESTERASES OF INTEREST | | | | | | |
| THA | 240–10 | 180–60 | 190–40 | 76–25 | 45–10 | 47–10 |
| DFP | 44–18 | 58–42 | 76–48 | 480–400 | 4.9–2.8 | 0.20–0.03 |
| BW284c51 | 28–12 | 22–8 | 18–8 | 7.3–0.4 | 300,000–270,000 | 48,000 |
| iso-OMPA | 180,000 | 250,000 | 340,000 | >1,000,000 | 6,700–4,100 | 980–550 |
| Ethoprop | 210,000 | 180,000 | 260,000 | 120,000 | 210 | 300 |
| Butyl | | | | | | |
| Chlorophenyl | | | | | | |
| Methoxyphenyl | | | | | | |
| $N^1$—Bn | | | | | | |
| $N^1$—Allyl | | | | | | |
| $N^1$—Phenethyl | | | | | | |
| $N^1$—H | | | | | | |

It was found that the addition of either a methoxy or a chloride group (YU-114 and 116, respectively), reduces the antiacetylcholinesterase potency of the unsubstituted derivative (YU-79) by approximately 10-fold (note—the IC50 for YU-79, 114, and 116 are approximately 30, 300, and 500 nmol, respectively). However, although the antibutyrylcholinesterase activity of the cholorophenyl derivative, YU-116 is similar to that of the unsubstituted compound YU-79, and is much less against acetylcholinesterase, the addition of a methoxy group, as in YU-114 increases the antibutyrylcholinesterase potency of the unsubstituted compound ten-fold. Whereas YU-79 and YU-116 are relatively specific for acetyl- rather than butyryl-cholinesterase, YU-114 is approximately equally potent against both enzymes.

Shortening the side chain of the octyl derivative, YU-71 to give the butyl derivative, YU-120, does not alter the potency of the compound against either acetyl- or butyryl-cholinesterase.

Of the compounds with modified ring structures the nor-, allyl-, and methosulfate derivatives of physostigmine (YU-96, 110, and 117, respectively) were all as potent against acetylcholinesterase as physostigmine itself. However, whereas YU-96 and YU-110 were equipotent versus both acetyl- and butyryl-cholinesterase, YU-117 was more potent against acetylcholinesterase than against butyrylcholinesterase.

The compounds of the present invention are useful as anticholinergic agents in all indications for which (−)-physostigmine is used medically, including glaucoma, myasthenia gravis, Alzheimer's disease, and antidotes for organophosphate poisoning. The compounds can be administered in the form of their pharmaceutically acceptable water-soluble salts such as fumarates, salicylates, oxalates, and the like. The compounds can be administered in any pharmaceutically acceptable amount, for example, in amounts ranging from about 0.001 g to about 1 g per Kg of body weight. Compositions within the scope of the invention include compositions wherein the active ingredient is contained in an effective amount to achieve its intended purpose. Based on information here presented, determination of the effective amounts is within the skill of the art.

In addition to the physostigmine derivatives of the present invention, these pharmaceutical compositions may contain suitable pharmaceutically acceptable carriers comprising excipients and auxiliaries which facilitate processing of the active compounds into preparations which can be used pharmaceutically. Preferably these preparations, which can be administered orally and which can be used for the preferred type of administration, such as tablets, dragees, and capsules, and also preparations which can be administered rectally, such as suppositories, as well as suitable solutions for administration by injection or orally, contain from about 0.1 to 99 percent, preferably from about 25–85 percent, of active ingredient, together with the excipient.

The pharmaceutical preparations of the present invention are manufactured in a known manner. For example, pharmaceutical preparations for oral use can be obtained by combining the active ingredients with solid excipients, optionally grinding the resulting mixture, and processing the mixture of granules along with suitable auxiliaries, if desired or necessary, to obtain tablets or dragee cores.

Suitable excipients are, in particular, fillers such as sugars, for example, lactose or sucrose, mannitol or sorbitol, cellulose preparations and/or calcium hydrogen phosphate, as well as binders such as starch paste using, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone. If desired, disintegrating agents may also be added, such as the above-mentioned starches as well as carboxymethyl starch, crosslinked polyvinylpyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, may be made resistant to gastric juices. For this purpose, concentrated sugar solutions may be used, which may optionally contain gum Arabic, talc, polyvinyl pyrrolidone, polyethylene glycol, and/or titanium dioxide, lacquer solutions, and suitable organic solvents or solvent mixtures. In order to produce coatings resistant to gastric juices, solutions of suitable cellulose preparations such as acetyl-cellulose phthalate or hydroxypropylmethylcellulose phthalate, are used. Dyestuffs or pigments may be added to the tablets or dragee coatings, for example, for identification or in order to characterize different combinations of doses of active ingredients. Delayed and extended release formulations can also be used.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and optional stabilizers.

In soft capsules, the active ingredients are preferably dissolved or suspended in suitable liquids, such as fatty oils liquid paraffin, or liquid polyethylene glycols. Stabilizers may also be used.

Pharmaceutical preparations which may be administered rectally include suppositories, which consist of a combination of the active compounds with a suppository base. Suitable suppository bases include natural or synthetic triglycerides, paraffin hydrocarbons, polyethylene glycols, or higher alkanols. Additionally, it is also possible to use rectal gelatin capsules which consist of a combination of the active compounds with a base. Base materials include liquid triglycerides, polyethylene glycols, and paraffin hydrocarbons.

Suitable formulations for parenteral administration include aqueous solutions of the active compounds in water-soluble form, as the water-soluble salts, such as fumarates, oxalates, and salicyclates. In addition, suspensions of the active compounds as appropriate oily injection suspensions may be administered. Suitable lipophilic solvents or vehicles include fatty oils, such as sesame oil, or synthetic fatty acid esters, such as ethyl oleate or triglycerides. Aqueous injection suspensions may contain substances which increase the viscosity of the suspension, including, by way of example, sodium carboxymethyl cellulose, sorbitol, and/or dextran. Optionally, the suspension may also contain stabilizers.

Alternatively, the active ingredients may by formulated in liposomes, pharmaceutical compositions in which the active ingredient is contained either dispersed or variously present in corpuscles consisting of aqueous concentric layers adherent to lipidic layers.

The active ingredient may be present both in the aqueous layer and in the lipidic layer.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A compound of the formula:

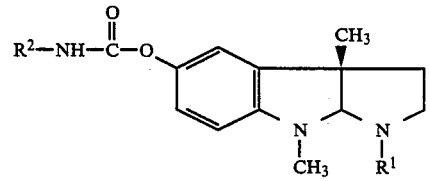

wherein
$R^1$=H, $R_2$=CH$_3$;
$R^1$=H, $R^2$=CH$_3$;
$R^1$=Bn, $R^2$=CH$_3$;
$R^1$=Bn, $R^2$=OH;
$R^1$=Bn, $R^2$=OCONH—CH$_3$;
$R^1$=H, $R^2$=CONH—CH$_3$;
$R^1$=CH$_2$=CH—CH$_2$, $R^2$=CONHCH$_3$; or
$R^1$=CH$_2$—CH$_2$—Ph, $R^2$=CONHCH$_3$.

2. A method of treating Alzheimer's disease comprising administering to a patient suffering from Alzheimer's disease an effective amount of a compound according to claim 1.

3. A method of treating myasthenia gravis comprising administering to a patient suffering from myasthenia gravis an effective amount of a compound according to claim 1.

4. A method for treating organophosphate poisoning comprising administering to a host which has been poisoned with organophosphates a compound according to claim 1.

5. A method for treating glaucoma comprising administering to a host afflicted with glaucoma an effective amount of a compound according to claim 1.

6. A method for inhibiting acetylcholinesterase and butylcholinesterase comprising administering to a patient in need of such therapy a therapeutically effective amount of a compound according to claim 1.

7. A method of inhibiting butyrylcholinesterase activity in a patient comprising administering to a patient in need of such therapy a therapeutically effective amount of a compound according to claim 1.

8. A composition for treating Alzheimer's disease comprising an effective amount of a compound according to claim 1 in a pharmaceutically acceptable carrier.

9. A composition for treating myasthenia gravis comprising an effective amount of a compound according to claim 1 in a pharmaceutically acceptable carrier.

10. A composition for treating organophosphate poisoning comprising an effective amount of a compound according to claim 1 in a pharmaceutically acceptable carrier.

11. A composition for treating glaucoma comprising an effective amount of a compound according to claim 1 in a pharmaceutically acceptable carrier.

12. A composition for inhibiting acetylcholinesterase activity comprising an effective amount of a compound according to claim 1 in a pharmaceutically acceptable carrier.

13. A composition for inhibiting butyrylcholinesterase activity comprising an effective amount of a compound according to claim 1 in a pharmaceutically acceptable carrier.

* * * * *

UNITED STATES PATENT AND TRADEMARK OFFICE
CERTIFICATE OF CORRECTION

PATENT NO. : 4,900,748  Page 1 of 2
DATED : February 13, 1990
INVENTOR(S) : Arnold BROSSI et al.

It is certified that error appears in the above-identified patent and that said Letters Patent is hereby corrected as shown below:

Column 2, line 67
Change "OH" to --H--.

Line 68, change "OCONH-CH$_3$" to --CONHCH$_3$--.

Column 3, line 2
Change "CONJCH$_3$" to --CONHCH$_3$--

IN THE CLAIMS: (counting the formula as one line)

Claim 1 Column 10, lines 25-31

Delete line 4.
Line 2, change

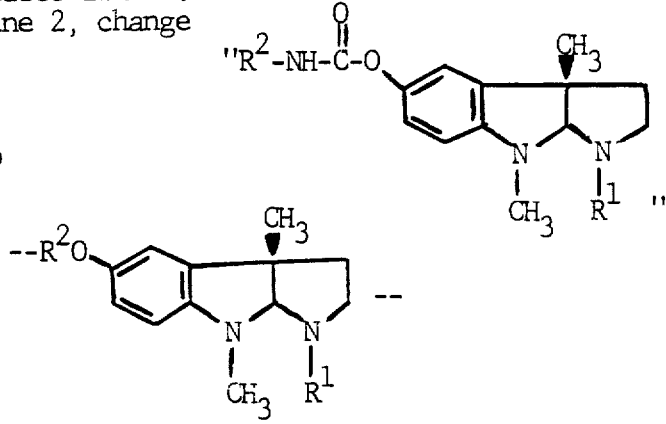

UNITED STATES PATENT AND TRADEMARK OFFICE
CERTIFICATE OF CORRECTION

PATENT NO. : 4,900,748

DATED : February 13, 1990

INVENTOR(S) : Arnold BROSSI et al.

It is certified that error appears in the above-identified patent and that said Letters Patent is hereby corrected as shown below:

COLUMN 10;

Line 7, change "OH" to --H--.

Line 8, change "OCONH-$CH_3$" to --CONHC$H_3$--.

After Line 10, insert --wherein Bn is benzyl--.

<u>Claim 4</u>

Line 3, after "organophosphates" insert --an effective amount of--.

Signed and Sealed this

Fourth Day of August, 1992

Attest:

DOUGLAS B. COMER

Attesting Officer     Acting Commissioner of Patents and Trademarks